United States Patent [19]

Lesher et al.

[11] 4,366,319

[45] Dec. 28, 1982

[54] PROCESS FOR PREPARING 5-(PYRIDINYL)BENZOXAZOL-2(3H)-ONES

[75] Inventors: George Y. Lesher, Shodack; Baldev Singh, East Greenbush, both of N.Y.

[73] Assignee: Sterling Drug Inc., New York, N.Y.

[21] Appl. No.: 273,480

[22] Filed: Jun. 15, 1981

Related U.S. Application Data

[62] Division of Ser. No. 209,416, Nov. 24, 1980, Pat. No. 4,310,531.

[51] Int. Cl.³ .......................................... C07D 263/58
[52] U.S. Cl. ..................................................... 546/270
[58] Field of Search ......................................... 546/270

[56] References Cited

PUBLICATIONS

Chem. Abstract 56:15516g.
Chem. Abstract 90:72191u.
Derwent Abstract 79163A/44, *J5 3111–062 on Japanese Patent 024432 (9-28-78).
Coates et al. [J. Chem. Soc. 1943, 406].
Heilbron et al. [J. Chem. Soc. 1940, 1279].

*Primary Examiner*—Ethel G. Love
*Attorney, Agent, or Firm*—Robert K. Bair; B. Woodrow Wyatt; Paul E. Dupont

[57] ABSTRACT

5-PY-benzoxazol-2(3H)-ones, cardiotonic agents, are prepared by reacting 2-amino-4-PY-phenol with a carbonylating agent, e.g., carbonyldiimidazole, where PY is 4- or 3-pyridinyl or 4- or 3-pyridinyl having one or two lower-alkyl substituents. 5-PY-benzoxazol-2(3H)-ones or pharmaceutically-acceptable acid-addition or cationic salts thereof are disclosed as active components in cardiotonic compositions for increasing cardiac contractility and in the method for increasing cardiac contractility in a patient requiring such treatment.

2 Claims, No Drawings

PROCESS FOR PREPARING 5-(PYRIDINYL)BENZOXAZOL-2(3H)-ONES

CROSS-REFERENCE TO RELATED APPLICATION

This is a division of application Ser. No. 209,416, filed Nov. 24, 1980, now U.S. Pat. No. 4,310,531, issued Jan. 12, 1982.

BACKGROUND OF THE INVENTION

The 2-amino-4-(pyridinyl)phenols used herein as intermediates are disclosed inter alia, as cardiotonics and claimed per se and as cardiotonics in copending U.S. Application Ser. No. 170,896, filed July 21, 1980, now U.S. Pat. No. 4,297,363, issued Oct. 27, 1981.

(a) Field of the Invention

This invention relates to (pyridinyl)benzoxazol-2-(3H)-ones, their preparation and their use as cardiotonics.

(b) Description of the Prior Art

Coates et al [J. Chem. Soc. 1943, 409] show the preparation of 4-(2-pyridinyl)-2-aminophenol in four steps from N-acetyl-4-(2-pyridinyl)aniline, the last two steps comprising converting 2-nitro-4-(2-pyridinyl)aniline to 2-nitro-4-(2-pyridinyl)phenol and reducing the latter to convert nitro to amino. Coates et al also show 3-(4-pyridinyl)phenol. Coates utilized said pyridinyl-phenols as intermediates to prepare pyridinyl-quinolines, which in turn were investigated for possible spasmolytic activity with disappointing results.

Heilbron et al [J. Chem. Soc. 1940, 1279] show as intermediates in the preparation of 3- and 4-pyridyl-diphenyls the following compounds: β-3-aminophenyl-pyridine, β-4-aminophenylpyridine and γ-4-aminophenylpyridine and the N-acetyl derivatives of each, including the hydrochloride and N-acetyl of β-4-acetamidophenylpyridine; these three aminophenylpyridines currently are named 3-(3-pyridinyl)benzeneamine, 4-(3-pyridinyl)benzeneamine and 4-(4-pyridinyl)benzeneamine, respectively, the two 4-(pyridinyl) isomers used as intermediates herein.

SUMMARY OF THE INVENTION

In a composition of matter aspect, the invention resides in a 5-(pyridinyl)benzoxazol-2(3H)-one or salt thereof, useful as a cardiotonic agent.

In a process aspect, the invention resides in the process which comprises reacting 2-amino-4-(pyridinyl)-phenol with a carbonylating agent to produce 5-(pyridinyl)benzoxazol-2(3H)-one.

In a composition aspect, the invention resides in a cardiotonic composition for increasing cardiac contractility which comprises a pharmaceutically-acceptable carrier and, as the active component thereof, a cardiotonically-effective amount of a 5(pyridinyl)benzoxazol-2(3H)-one or salt.

In a method aspect, the invention resides in a method for increasing cardiac contractility in a patient requiring such treatment which comprises administering to such patient a cardiotonically-effective amount of a 5-(pyridinyl)benzoxazol-2(3H)-one or salt.

DETAILED DESCRIPTION INCLUSIVE OF PREFERRED EMBODIMENTS

In a composition of matter aspect, the invention resides in 5-PY-benzoxazol-2-(3H)-one having formula I

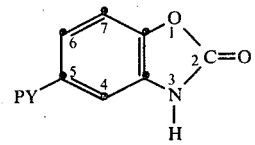

or pharmaceutically-acceptable acid-addition or cationic salt thereof where PY is 4- or 3-pyridinyl or 4- or 3-pyridinyl having one or two lower-alkyl substituents. These compounds are useful as cardiotonic agents, as determined by standard cardiotonic evaluation procedures. Preferred embodiments are the compounds of formula I where PY is 4-pyridinyl and 3-pyridinyl or said salt thereof.

In a process aspect, the invention resides in the process which comprises reacting 2-amino-4-PY-phenol with a carbonylating agent, preferably carbonyldiimidazole, to produce 5-PY-benzoxazol-2(3H)-one of formula I, where Py is 4- or 3-pyridinyl or 4- or 3-pyridinyl having one or two lower-alkyl substituents.

A composition aspect of the invention resides in the cardiotonic composition for increasing cardiac contractility which comprises a pharmaceutically-acceptable pharmaceutical carrier and, as the active component thereof, a cardiotonically-effective amount of 5-PY-benzoxazol-2(3H)-one or pharmaceutically-acceptable acid-addition or cationic salt thereof, where PY is 4- or 3-pyridinyl or 4- or 3-pyridinyl having one or two lower-alkyl substituents. Preferred embodiments of this aspect of the invention are the compositions having, as the active component, said compound where PY is 4- or 3-pyridinyl or said salt thereof.

A method aspect of the invention resides in the method for increasing cardiac contractility in a patient requiring such treatment which comprises administering orally or parenterally in a solid or liquid dosage form to such patient a cardiotonically-effective amount of 5-PY-benzoxazol-2(3H)-one or pharmaceutically-acceptable acid-addition or cationic salt thereof, where PY is 4- or 3-pyridinyl or 4- or 3-pyridinyl having one or two lower-alkyl substituents, a preferred embodiment being the method using said compound where PY is 4- or 3-pyridinyl.

The term "lower-alkyl" as used herein, e.g., as the meaning of the substituent for PY means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compound of formula I is useful both in the free base form and in the form of acid-addition salts, and, both forms are within the purview of the invention. The acid addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. Appropriate pharmaceutically-acceptable salts within the scope of the invention are those derived from mineral acids such as hydrochloric acid, hydrobromic acid, sulfuric acid, phosphoric acid and sulfamic acid; and organic acid such as lactic acid, acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compound of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound of formula I are preferred, all acid-addition salts are within the scope of the invention. All acid-addition salts are useful as sources of the free base from even if the particular salt per se is desired only as an intermediate product as for example when the salt is formed only for purposes of purification or identification, or when it is used as an intermediate in preparing a pharmaceutically-acceptable salt by ion exchange procedures.

Other pharmaceutically-acceptable salts of said compound of formula I are those cationic salts derived from strong inorganic or organic bases, e.g., sodium hydroxide, potassium hydroxide, trimethylammonium hydroxide, to produce the corresponding 1- or N- cationic salt, e.g., sodium, potassium, trimethylammonium salt, respectively, that is, the cationic ion being attached to the 1- or N-position of the 2(1H)-pyridinone ring.

The molecular structures of the 5-PY-benzoxazol-2(3H)-ones were assigned on the basis of evidence provided by infrared, ultraviolet, nuclear magnetic resonance and mass spectra, by chromatographic mobilities, by the correspondence of calculated and found values for the elemental analyses, and, by their method of preparation.

The manner of making and using the instant invention will now be generally described so as to enable a person skilled in the art of pharmaceutical chemistry to make and use the same, as follows.

The reaction of 2-amino-4-PY-phenol with a carbonylating agent to produce 5-PY-benzoxazol-2(3H)-one is carried out by mixing the reactants in a suitable inert aprotic solvent at room temperature or heating the reaction mixture up to about 100° C. The reaction was conveniently run by stirring the reactants, preferably using carbonyldiimidazole as the carbonylating agent, at room temperature in dimethylformide. Other suitable solvents include dioxane, tetrahydrofuran, toluene, and the like. Instead of using carbonyldiimidazole as the carbonylating agent, that is, an agent providing carbonyl, there can be used a di-(lower-alkyl) carbonate, e.g., diethyl or dimethyl carbonate, a lower-alkyl, ethyl or methyl, chloroformate or phosgene: when said alkyl chloroformate or phosgene is used as the carbonylating agent, an acid-acceptor, e.g., triethylamine, pyridine, sodium or potassium hydroxide, sodium or potassium carbonate, and the like, should be used to take up the hydrogen chloride formed as a by-product by the reaction. The preparation of 5-PY-benzoxazol-2(3H)-ones is illustrated below in Examples D-1 through D-7.

The preparation of the intermediate 2-amino-4-PY-phenols and the intermediates used therein are presented in the following three paragraphs.

The reaction of 2-nitro-4-PY-phenol with a reducing agent to produce 2-amino-4-PY-phenol was conveniently carried out either by catalytic or chemical reductive means. In practicing the invention, this reduction was conveniently run in a suitable solvent, e.g., acetic acid, dimethylformamide, in the presence of a hydrogenation catalyst, e.g., platinum oxide, palladium-on-charcoal, under catalytic hydrogenation conditions at ambient temperature (about 20° to 25° C.) until the uptake of hydrogen ceased. Other suitable solvents include tetrahydrofuran, dioxane, methanol, ethanol, water (containing a base, e.g., sodium hydroxide, potassium hydroxide, triethylamine, etc.), and the like. Other suitable hydrogenation catalysts include Raney nickel, and the like. Chemical reducing agents useful in the reduction of the 2-nitro compound to produce the 2-amino compound include iron and acetic acid, zinc and hydrochloric acid, and the like. The preparation of the 2-amino-4-PY-phenols is illustrated hereinbelow in Examples C-1 through C-7.

The intermediate 2-nitro-4-PY-phenols are prepared by nitrating the generally known 4-PY-phenols by conventional nitrating procedures, as illustrated hereinbelow in Examples B-1 through B-7.

The generally known 4-PY-phenols are conveniently prepared by the generally known procedures of converting corresponding 4-PY-benzenamines via aqueous hydrolysis of their diazonium salts, as illustrated hereinbelow in Examples A-1 through A-7. Illustrative of a known 4-PY-phenol is 4-(4-methyl-3-pyridinyl)phenol [Chem. Abstrs. 81, 25,571x (1974)].

Illustrative of known 4-PY-benzeneamines are 4-(4-pyridinyl)benzeneamine [Forsyth et al. J. Chem. Soc. 1926, 2912 and Heilbron et al., J. Chem. Soc. 1940, 1279], 4-(3-pyridinyl)benzeneamine [Heilbron et al, ibid.] and 4-(2,5-dimethyl-4-pyridinyl)benzeneamine [Prostakov et al., Chem. Abstr. 84, 179, 989p (1976)], which are prepared from the corresponding known 4-PY-nitrobenzenes. Illustrative of another known 4-PY-nitrobenzene is 4-(2-methyl-4-pyridinyl)nitrobenzene [Agrawal et al., J. Med. Chem. 18, 368 (1975)], which is prepared, inter alia, by nitrating 4-phenyl-2-picoline.

The following examples will further illustrate the invention without, however, limiting it thereto.

A. 4-PY-PHENOLS—These intermediates are prepared by the generally known procedure of converting the corresponding generally known 4-PY-benzeneamine to its diazonium salt and then converting the salt to the desired 4-PY-phenol, as illustrated below in Examples A-1 through A-7.

A-1. 4-(4-Pyridinyl)phenol—To an ice cold stirred mixture containing 85 g. of 4-(4-pyridinyl)benzeneamine, 250 ml. of concentrated sulfuric acid and 1 liter of water was added with stirring over a period of 2 hours a solution containing 35 g. of sodium nitrite in 100 ml. of water, keeping the reaction temperature below 5° C. during the addition. The resulting dark solution was left room temperature overnight and then filtered. The filtrate was heated on a steam bath for 4 hours, treated with decolorizing charcoal and filtered. The filtrate was chilled in an ice bath and was neutralized by adding concentrated ammonium hydroxide. The resulting yellow precipitate was collected, washed with water and dried at 80° C. to yield 75.8 g. of 4-(4-pyridinyl)phenol, m.p. 240°–244° C.

Following the procedure described in Example A-1 but using a molar equivalent quantity of the appropriate 4-PY-benzeneamine in place of 4-(4-pyridinyl)benzeneamine, it is contemplated that the corresponding 4-PY-phenols of Examples A-2 thru A-7 can be obtained.

A-2. 4-(3-Pyridinyl)phenol, using 4-(3-pyridinyl)benzeneamine.

A-3. 4-(2-Methyl-4-pyridinyl)phenol, using 4-(2-methyl-4-pyridinyl)benzeneamine.

A-4. 4-(2,6-Dimethyl-4-pyridinyl)phenol, using 4-(2,6-dimethyl-4-pyridinyl)benzeneamine.

A-5. 4-(2,5-Dimethyl-3-pyridinyl)phenol, using 4-(2,5-dimethyl-3-pyridinyl)benzeneamine.

A-6. 4-(4-Methyl-3-pyridinyl)phenol, using 4-(4-methyl-3-pyridinyl)benzeneamine.

A-7. 4-(2-Ethyl-4-pyridinyl)phenol, using 4-(2-ethyl-4-pyridinyl)benzeneamine.

B. 2-NITRO-4-PY-PHENOLS

B-1. 2-Nitro-4-(4-pyridinyl)phenol—To a stirred mixture containing 51.3 g. of 4-(4-pyridinyl)phenol and 500 ml. of acetic acid cooled in an ice cold water bath was added over 20 minute period a solution containing 15 ml. of concentrated nitric acid in 50 ml. of acetic acid. The resulting mixture was heated gently with stirring on a steam bath for 4 hours and then allowed to stand at ambient temperature over the weekend the resulting reaction mixture was heated in vacuo to distill off about 400 ml. of acetic acid. To the residue was added 300 ml. of water and 75 ml. of concentrated ammonium hydroxide. The solid that separated was collected, washed with water and dried at 80° C. to yield 61.2 g. of 2-nitro-4-(4-pyridinyl)phenol, m.p. 210°–212° C.

Following the procedure described in Example B-1, but using a molar equivalent quantity of the appropriate 4-PY-phenol in place of 4-(4-pyridinyl)-phenol, it is contemplated that the corresponding 2-nitro-4-PY-phenols of Examples B-2 thru B-7 can be obtained.

B-2. 2-Nitro-4-(3-pyridinyl)phenol, using 4-(3-pyridinyl)phenol.

B-3. 2-Nitro-4-(2-methyl-4-pyridinyl)phenol, using 4-(2-methyl-4-pyridinyl)phenol.

B-4. 2-Nitro-4-(2,6-dimethyl-4-pyridinyl)phenol, using 4-(2,6-dimethyl-4-pyridinyl)phenol.

B-5. 2-Nitro-4-(2,5-dimethyl-3-pyridinyl)phenol, using 4-(2,5-dimethyl-3-pyridinyl)phenol.

B-6. 2-Nitro-4-(4-methyl-3-pyridinyl)phenol, using 4-(4-methyl-3-pyridinyl)phenol.

B-7. 2-Nitro-4-(2-ethyl-4-pyridinyl)phenol, using 4-(2-ethyl-4-pyridinyl)phenol.

C. 2-AMINO-4-PY-PHENOLS

C-1. 2-Amino-4-(4-pyridinyl)phenol—A mixture containing 21.6 g. of 2-nitro-4-(4-pyridinyl)phenol, 175 ml. of acetic acid, 25 ml. of water and 1 g. of platinum dioxide was shaken with hydrogen under catalytic hydrogenation conditions until the required amount of hydrogen was taken up. The catalyst was filtered off and to the filtrate was added 100 ml. of concentrated hydrochloric acid and the mixture was heated in vacuo to dryness. The residue was stirred with methanol and the product collected, dried at 90° C. to yield 22.4 g. of 2-amino-4-(4-pyridinyl)phenol as its dihydrochloride, m.p. >300° C.

Other acid-addition salts of 2-amino-4-(4-pyridinyl)phenol are conveniently prepared by adding to a mixture of 1 g. of 2-amino-4-(4-pyridinyl)phenol in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring a molar equivalent quantity each of 2-amino-4-(4-pyridinyl)phenol and the appropriate acid, e.g., lactic acid or hydrochloric acid, to prepare respectively the lactate or hydrochloride salt of 2-amino-4-(4-pyridinyl)phenol in aqueous solution.

Following the procedure described in Example C-1 but using a molar equivalent quantity of the appropriate 2-nitro-4-PY-phenol in place of 2-nitro-4-(4-pyridinyl)-phenol, it is contemplated that the corresponding 2-amino-4-PY-phenols of Examples C-2 thru C-7 can be obtained.

C-2. 2-Amino-4-(3-pyridinyl)phenol

C-3. 2-Amino-4-(2-methyl-4-pyridinyl)phenol

C-4. 2-Amino-4-(2,6-dimethyl-4-pyridinyl)phenol

C-5. 2-Amino-4-(2,5-dimethyl-3-pyridinyl)phenol

C-6. 2-Amino-4-(4-methyl-3-pyridinyl)phenol

C-7. 2-Amino-4-(2-ethyl-4-pyridinyl)phenol

D. 5-PY-BENZOXAZOL-2(2H)-ONES

D-1. 5-(4-Pyridinyl)benzoxazol-2(3H)-one—A mixture containing 18.6 g. of 2-amino-4-(4-pyridinyl)phenol, 200 ml. of dimethylformamide and 18.9 g. of N,N'-carbonyldiimidazole was stirred at room temperature for 18 hours and then concentrated on a rotary evaporator to remove the solvent. The residue was diluted with 200 ml. of water and the precipitate was collected and air-dried. The solid was dissolved in about 400 ml. of boiling isopropyl alcohol and the hot solution treated with decolorizing charcoal and filtered. The filtrate was concentrated to a volume of about 75 ml. and allowed to cool. The crystalline precipitate was collected and dried at 80° C. to yield 12.9 g. of 5-(4-pyridinyl)benzoxazol-2(3H)-one, m.p. 223°–225° C.

Acid-addition salts of 5-(4-pyridinyl)benzoxazol-2(3H)-one are conveniently prepared by adding to a mixture of 1 g. of 5-(4-pyridinyl)benzoxazol-2(3H)-one in about 20 ml. of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 5-(4-pyridinyl)benzoxazol-2(3H)-one and the appropriate acid, e.g., lactic acid or hydrochloric acid, to prepare respectively the lactate or hydrochloride salt of 5-(4-pyridinyl)benzoxazol-2(3H)-one in aqueous solution.

Following the procedure described in Example D-1 but using a molar equivalent quantity of the appropriate 2-amino-4-PY-phenol in place of 2-amino-4-(4-pyridinyl)phenol, it is contemplated that the corresponding 5-PY-benzoxazol-2(3H)-ones of Examples D-2 thru D-7 can be obtained.

D-2. 5-(3-Pyridinyl)benzoxazol-2(3H)-one, using 2-amino-4-(3-pyridinyl)phenol.

D-3. 5-(2-Methyl-4-pyridinyl)benzoxazol-2(3H)-one, using 2-amino-4-(2-methyl-4-pyridinyl)phenol.

D-4. 5-(2,6-Dimethyl-4-pyridinyl)benzoxazol-2(3H)-one, using 2-amino-4-(2,6-dimethyl-4-pyridinyl)phenol.

D-5. 5-(2,5-Dimethyl-3-pyridinyl)benzoxazol-2(3H)-one, using 2-amino-4-(2,5-dimethyl-3-pyridinyl)phenol.

D-6. 5-(4-Methyl-3-pyridinyl)benzoxazol-2(3H)-one, using 2-amino-4-(4-methyl-3-pyridinyl)phenol.

D-7. 5-(2-Ethyl-4-pyridinyl)benzoxazol-2(3H)-one, using 2-amino-4-(2-ethyl-4-pyridinyl)phenol.

The usefulness of the 5-PY-benzoxazol-2(3H)-one of formula I salt as cardiotonic agent is demonstrated by its effectiveness in standard pharmacological test procedures, for example, in causing a significant increase in the contractile force of the isolated cat atria and papillary muscle and in causing a significant increase in cardiac contractile force in the anesthetized dog with low or minimal changes in heart rate and blood pressure. These test procedures are described in U.S. Pat. No. 4,072,746, issued Feb. 7, 1978.

When tested by the above-noted isolated cat atria and papillary muscle procedure the compounds of formula I or salts at doses of 10, 30 or 100 $\mu$g./ml. were found to cause a significant increase, that is, greater than 25%, in papillary muscle force and a significant increase, that is, greater than 25%, in right atrial force, while causing a lower percentage increase (than that of papillary muscle force and right atrial force) in right atrial rate. For example, 5-(4-pyridinyl)benzoxazol-2(3H)-one when tested by said isolated cat atria and papillary muscle procedure was found to cause 86%, 77% and 179% increases in papillary muscle force at 10, 30 and 100 $\mu$g./ml., respectively, and to cause 76%, 86% and 188% increases in right atrial force at the same respective doses.

The present invention includes within its scope a cardiotonic composition for increasing cardiac contractility, said composition comprising a pharmaceutically-acceptable carrier and, as the active component thereof, a cardiotonically-effective amount of 5-PY-benzoxazol-2(3H)-one or pharmaceutically-acceptable acid-addition or cationic salt thereof. The invention also includes within its scope the method for increasing cardiac contractility in a patient requiring such treatment which comprises administering to such patient a cardiotonically-effective amount of said 5-PY-benzoxazol-2(3H)-one or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in said composition and method for increasing cardiac contractility may be varied to that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. The process which comprises reacting 2-amino-4-PY-phenol with carbonyldiimidazole to produce 5-PY-benzoxazol-2(3H)-one where PY is 4- or 3-pyridinyl or 4- or 3-pyridinyl having one or two lower-alkyl substituents.

2. The process according to claim 1 where PY is 4- or 3-pyridinyl.

* * * * *